(12) United States Patent
Pastine

(10) Patent No.: US 8,785,694 B2
(45) Date of Patent: Jul. 22, 2014

(54) PROCESSES FOR THE PREPARATION OF DI-(2-AMINOETHYL) FORMAL, DI-(3-AMINOPROPYL) FORMAL, AND RELATED MOLECULES

(71) Applicant: Stefan J. Pastine, San Francisco, CA (US)

(72) Inventor: Stefan J. Pastine, San Francisco, CA (US)

(73) Assignee: Connora Technologies, Inc, Hayward, CA (US)

( * ) Notice: Subject to any disclaimer, the term of this patent is extended or adjusted under 35 U.S.C. 154(b) by 0 days.

(21) Appl. No.: 13/910,612

(22) Filed: Jun. 5, 2013

(65) Prior Publication Data

US 2013/0324764 A1     Dec. 5, 2013

Related U.S. Application Data

(60) Provisional application No. 61/655,794, filed on Jun. 5, 2012.

(51) Int. Cl.
*C07C 209/48*     (2006.01)

(52) U.S. Cl.
USPC .......................................................... 564/491

(58) Field of Classification Search
USPC .......................................................... 564/491
See application file for complete search history.

(56) References Cited

U.S. PATENT DOCUMENTS 2,409,675 A * 10/1946 Gresham ........................ 564/474

* cited by examiner

*Primary Examiner* — Brian J Davis
(74) *Attorney, Agent, or Firm* — Morgan, Lewis & Bockius LLP

(57) ABSTRACT

Disclosed herein are hardeners for use in making cleavable epoxy compositions, including compositions wherein components in contact with epoxy composition can be recovered, as well as methods of making such hardeners.

22 Claims, 2 Drawing Sheets

PROCESSES FOR THE PREPARATION OF DI-(2-AMINOETHYL) FORMAL, DI-(3-AMINOPROPYL) FORMAL, AND RELATED MOLECULES

CROSS-REFERENCE TO RELATED APPLICATION

The present application claims priority benefit from U.S. Provisional Application No. 61/655,794, filed 5 Jun. 2012, the contents of which is incorporated herein by reference in its entirety.

BACKGROUND

The present invention generally relates to the art of thermosetting plastics, epoxy resins, and epoxy resin curing agents, and the hardeners used in the preparation of such compositions.

BRIEF SUMMARY OF THE INVENTION

In one embodiment, the present invention provides a process chemical synthesis for the preparation of di-(2-aminoethyl) formal acetal of formula I. In one embodiment, the process comprises reacting a compound of formula Va with a second compound selected from the group consisting of ammonia, ammonium salt, and combinations or equivalents (such as ammonium hydroxide) thereof, to form di-(2-aminoethyl) formal acetal of formula I:

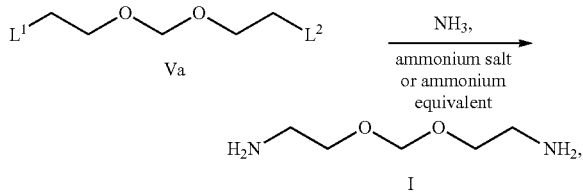

wherein $L^1$ and $L^2$ are the same or different and each is independently a leaving group or leaving group precursor. In one embodiment, each of $L^1$ and $L^2$ is independently selected from the group consisting halogen or an alkyl- or aryl-sulfonyloxy group. In one embodiment, each of $L^1$ and $L^2$ is independently selected from the group consisting of a chloro, a bromo, an iodo, a mesyloxy, a besyloxy and a tosyloxy group. In one embodiment, each of $L^1$ and $L^2$ is independently selected from the group consisting of a halide, methanesulfonate, para-toluenesulfonate, trifluoromethane sulfonate, mono nitro and dinitro phenolate.

In some embodiments, the process chemical synthesis for the preparation of di-(2-aminoethyl) formal acetal of formula I further comprises adding an additive to the reaction. In one embodiment, the additive is an iodide salt. In one embodiment, the iodide salt is a potassium iodide or a sodium iodide or a combination of both.

In some embodiments, the process chemical synthesis for the preparation of di-(2-aminoethyl) formal acetal of formula I, the reaction is conducted at a temperature range of from about 0° C. to 200° C. In one embodiment, the reaction is conducted at a temperature range of from about 40° C. to 140° C. In one embodiment, the reaction is optionally conducted in the presence of a solvent. In one embodiment, the solvent is selected from the group consisting of water, methanol, ethanol, dioxane and combinations thereof.

In some embodiments, the process chemical synthesis for the preparation of di-(2-aminoethyl) formal acetal of formula I, the reaction is conducted in a pressurized system. In one embodiment, the reaction is conducted in the presence of excess ammonia or ammonia equivalents. In one embodiment, the molar proportion of the ammonia or ammonia equivalents to the compound of formula Va is about 20:1. In one embodiment, the molar proportion of the ammonia or said ammonia equivalents to the compound of formula Va is greater than about 20:1. In one embodiment, the molar proportion of the ammonia or the ammonia equivalents to the compound of formula Va is less than about 20:1.

In some embodiments, the process of chemical synthesis for the preparation of di-(2-aminoethyl) formal acetal of formula I comprises reducing di-(2-nitroethyl) formal acetal Vb with a reducing agent to form the compound formula I:

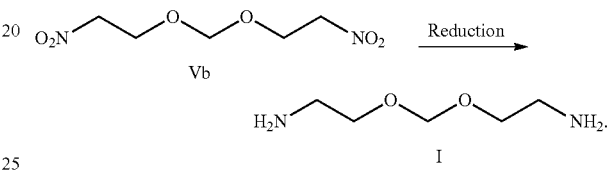

In one embodiment, the reducing agent is hydrogen gas in the presence of a catalyst. In one embodiment, the reducing agent is selected from the group consisting of hydrogen in the presence of catalytic Raney nickel, hydrogen in the presence of catalytic Palladium on carbon (Pd/C), catalytic Pd/C and ammonium formate in methanol, hydrogen in the presence of catalytic $PtO_2$, iron metal in the presence of acid, and iron metal/$FeCl_3$ in the presence of acid. In one embodiment, the hydrogenation catalyst is recovered and recycled. In one embodiment, the hydrogenation catalyst is recovered via filtration after the reaction is complete. In one embodiment, the reaction is conducted at a temperature range of from about 20° C. to 200° C. In one embodiment, the reaction is conducted at a temperature range of from about 40° C. to 140° C. In one embodiment, the reaction is conducted under hydrogen gas pressure of from about 1 atm to about 1000 atm.

In some embodiments, the process of chemical synthesis for the preparation of di-(2-aminoethyl) formal acetal of formula I comprises reacting ethanolamine with paraformaldehyde or any suitably masked formaldehyde equivalent in the presence of an acid to form di-(2-aminoethyl) formal acetal salt of formula VIII; and reacting said di-(2-aminoethyl) formal acetal salt VII with a base to form di-(2-aminoethyl) formal acetal I:

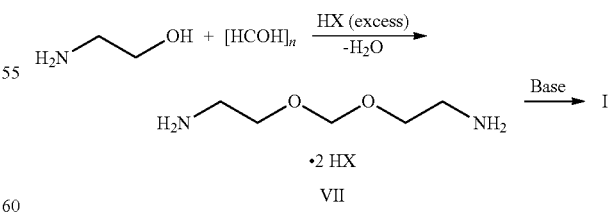

In one embodiment, the acid is an inorganic acid. In one embodiment, the acid is selected from the group consisting of HCl, HBr and $H_2SO_4$. In one embodiment, the acid is an organic acid. In one embodiment, the organic acid is p-toluenesulfonic acid, acetic acid or methanesulfonic acid. In one embodiment, the suitably masked formaldehyde equivalent is trioxane. In one embodiment, the ratio of a molar equivalence of the acid to ethanolamine is greater than 1. In one embodiment, the ethanolamine is pretreated with an acid prior to the reaction with the paraformaldehyde or the any suitably masked formaldehyde equivalent. In one embodiment, the process further comprises the step of adding a drying agent to the reaction mixture. In one embodiment, the drying agent is anhydrous magnesium sulfate ($MgSO_4$). In one embodiment, the drying agent is anhydrous sodium sulfate ($Na_2SO_4$) or anhydrous potassium sulfate ($K_2SO_4$). In one embodiment, the process is conducted under Dean-Stark type reaction condition to remove any water formed during the reaction. In one embodiment, the process is conducted at temperature ranging from about 0° C. to about 220° C.

In some embodiments, the process of chemical synthesis for the preparation of di-(2-aminoethyl) formal acetal of formula I comprises reacting ethanolamine with a formylacetal of formula VIII to form di-(2-aminoethyl) formal acetal salt of formula VII; and reacting the di-(2-aminoethyl) formal acetal salt of formula VII with a base to form di-(2-aminoethyl) formal acetal of formula I:

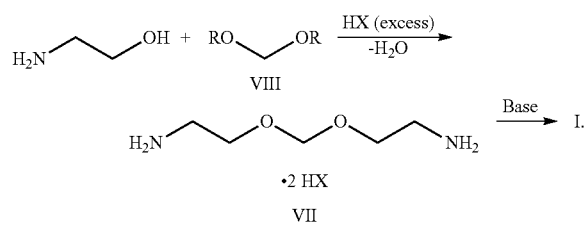

In some embodiments, the present invention provides a process of chemical synthesis for the preparation of di-(3-aminopropyl) formal acetal of formula X. In one embodiment, the process comprises a catalytic hydrogenation reaction of a compound of formula IX:

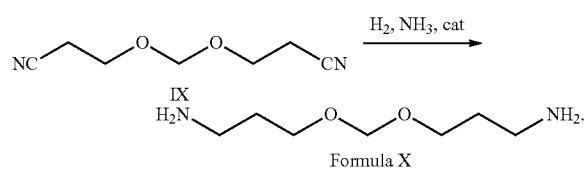

DETAILED DESCRIPTION

Figure 1:
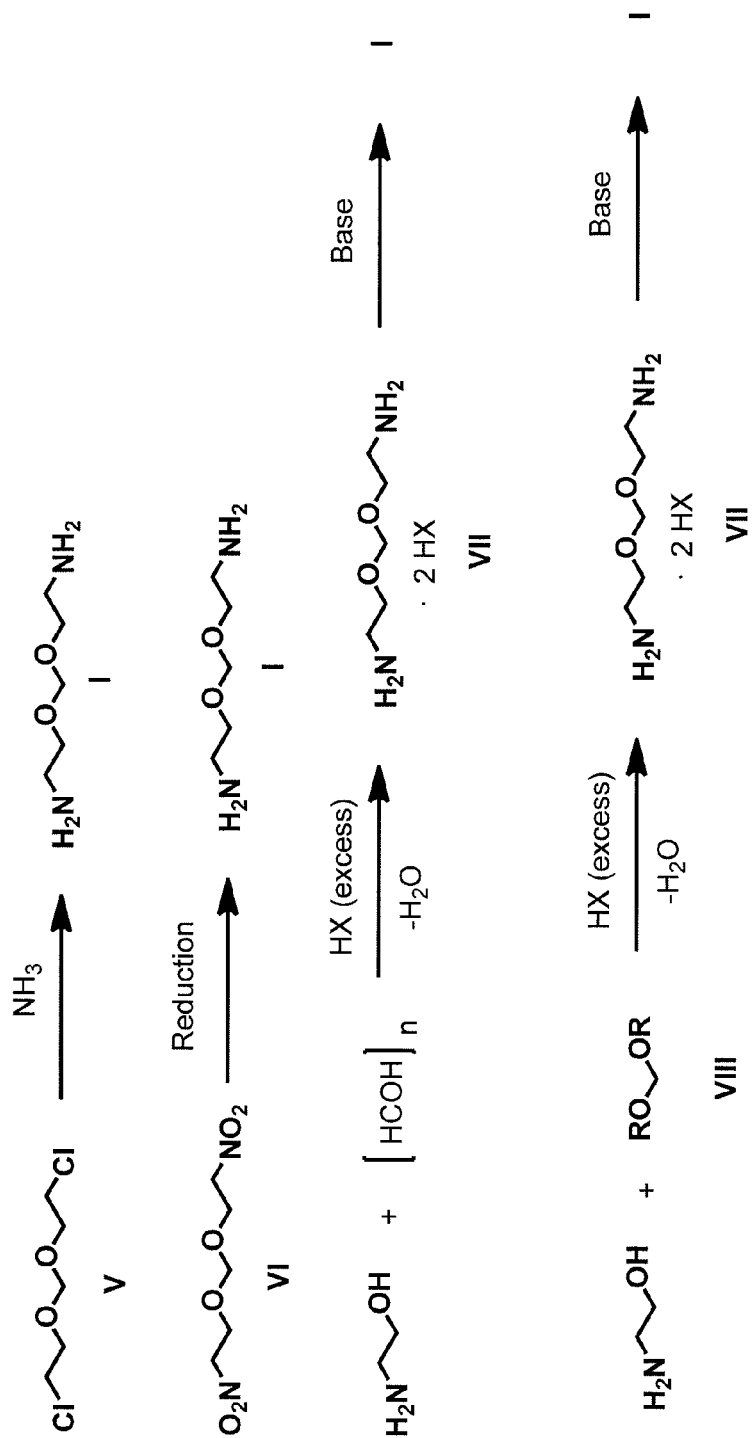
FIG. 1 is an image depicting di(ethylamino)formal synthetic routes of the present disclosure.
Figure 2:
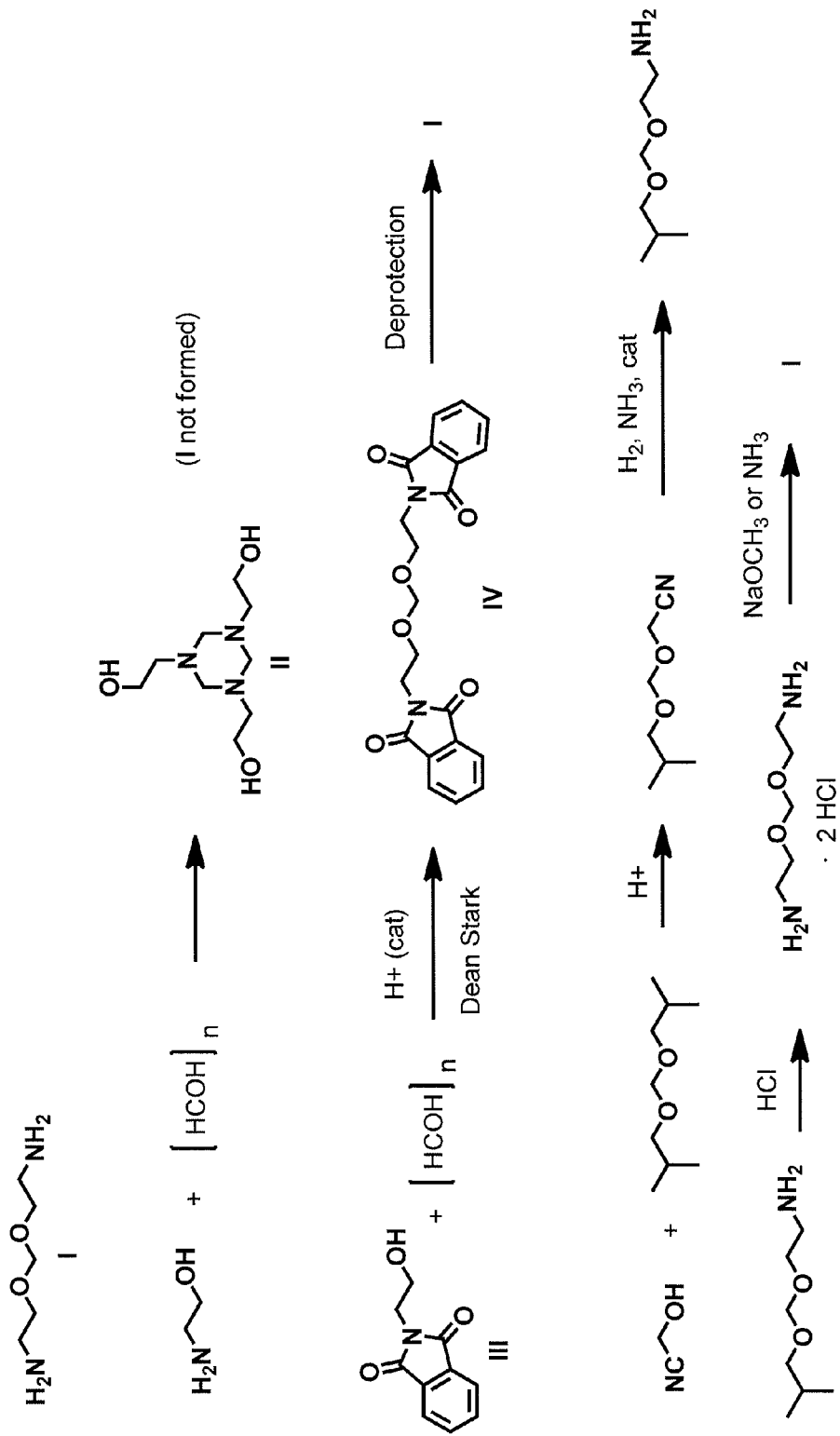
FIG. 2 is an image depicting di(ethylamino)formal synthetic routes of the present disclosure.

Epoxies are an important class of thermosetting polymers. Epoxy resins are typically hardened or cured by a cross-linking reaction using one of three general methods. The chemistry of epoxy curing is explained in great detail in the Handbook of Composites (edited by S. T. Peters, Chapter 3, pp 48-74, published by Chapman & Hall, 1998). The properties and applications of cured resin are greatly influenced by the choice of the hardener formulation or the method of curing.

One method is simply the reaction of the epoxy resin with itself (i.e. homopolymerization) via a ring-opening polymerization mechanism of the epoxy groups. The self-curing of epoxy resins usually requires an elevated temperature but can be initiated with either a Lewis acid- or a Lewis base catalyst (as opposed to a curing agent).

In the second method, the epoxy resin is cured with a cyclic acid anhydride. The anhydride can react with the epoxy group, pendant hydroxyls, or residual water to form a carboxylate intermediate, which then reacts with the epoxy group, causing a self-perpetuating reaction between the anhydride and the epoxy resin. Catalytic amounts of tertiary amines are commonly used as additives as they facilitate the opening of the anhydride. Typically, anhydride epoxy formulations generally do not readily cure at room temperature, and are generally cured at elevated temperatures.

In the third method, the epoxy resin reacts with polyvalent nucleophiles such as polyamines to form a polymeric network of essentially infinite molecular weight. Epoxy groups will react with potentially every amine containing an active hydrogen atom, so that a simple diamine ($NH_2$—R—$NH_2$) acts as a tetra-functional cross-linker, reacting with four epoxy groups. The ring opening of the epoxy ring with a primary or secondary amine generates a stable C—N bond, and the reaction is essentially irreversible. Aliphatic polyamines are widely used in ambient temperature curing compositions. Aromatic amines are generally less reactive than aliphatic amines, so they are primarily used in elevated temperature curing compositions. The use of aromatic diamine hardeners such as 4,4'-methylenedianiline (MDA) or 4,4'-diaminodiphenyl sulfone (DDS) are commonly used in epoxy applications that require enhanced temperature properties such as high glass transition temperature (Tg) or in composite manufacturing techniques that require long pot-life at ambient temperature such as a pre-impregnated ("prepreg") method, wherein, for example, composite fibers may already have a material such as an epoxy present.

Epoxies serve massive global markets in adhesives and coatings, and are also one of the industry standard thermosetting plastic matrices used for construction of fiber reinforced plastic (FRP). FRPs are composite materials consisting of a polymer matrix and a fiber such as carbon fiber, fiberglass, aramid fiber, natural fiber, or other fiber. The fiber serves to enhance the properties of the plastic in areas such as strength and elasticity. FRPs are also commonly referred to as "plastic composites" or, for simplicity, just "composites." The term "plastic composites" can also embody plastic materials that have non-fibrous entities incorporated in them such as metals or nanomaterials. Plastic composites provide lightweight alternatives to other structural materials (e.g., steel or aluminum) and are widely used in the automotive, aerospace, nautical craft, wind energy, and sporting goods sectors. The incorporation of lightweight composites can offer substantial environmental benefits by way of leading to increased energy efficiency; yet, the positive impact of thermosetting plastic composites is offset by their lack of recyclability and persistence in the environment. The predicted waste accumulation in the growing wind power industry is an illustrious example. The current output of wind energy is approximately 10 times that of the production in 1980, and windmill blade propellers can reach over 60 meters in length. The material wastage from wind motor blade production is estimated to reach 225,000 tons per year by 2034. The weight percentage of epoxy in fiber reinforced epoxies typically is in the range of 25-40%. The raw materials (i.e. the plastic and fiber) that go into composite construction can be expensive, and are usually of petrochemical origins. Thus, there are both economic and environmental drivers for the development of new reworkable epoxy thermosetting compositions that would enable the manufacture of recyclable fiber reinforced epoxy composites.

Of the three general epoxy curing methods describe above, epoxy compositions based on diepoxides ("resin") and polyamines ("hardener") to form a cross-linked polymeric network of essentially infinite molecular weight are very common (the combination of "resin+hardener" is sometimes referred to as "cured epoxy" or "cured resin" or simply "resin" or epoxy). The widespread utility of such epoxy formulations for composite manufacturing and other structural applications is due to their generally excellent processablity prior to curing and their excellent post-cure adhesion, mechanical strength, thermal profile, chemical resistance, etc. Further, the high-density, three-dimensional network of epoxies makes epoxies robust materials, tolerant of a wide range of environmental conditions. At the same time, the cross-linked network makes the removal, recycling, and/or reworkability of epoxy, or epoxy-based materials, notoriously difficult. The cross-linking reactions that occur with conventionally used polyamine epoxies formulation are essentially irreversible; therefore, the material cannot be re-melted and re-shaped without decomposition; the material cannot be readily dissolved either. As a result, fiber reinforced epoxies or epoxy-based composite materials are not amenable to standard recycling practices because the epoxy matrix and fibers cannot be readily separated, and recovered. Thermosetting composites are typically disposed of in landfills, or by burning. An emerging technology for disposal of carbon fiber composites involves special incinerators burn away the plastic matrix of the composite, leaving behind the carbon fiber, which then can be reclaimed. However, the value of the thermoset matrix is not extracted in a repurposable from as it is destroyed in the incineration process.

The intractability of a cured epoxy resin stems, primarily, from its highly cross-linked network. Those in the art can understand that if the links in the three-dimensional network can be cleaved under controlled conditions, then the network can be disassembled into smaller, soluble molecules and/or polymers, and therefore the cured matrix can potentially be separated and recovered from the fiber in a composite. By providing for the manufacture of recyclable epoxy composites, components of the plastic matrix and components of the reinforcement material can be recovered by way of a recycling step. In principal, such type of recyclable epoxy compositions can be accomplished through use of either a dissolvable (or degradable) resin or a curing agent that contains a bond capable of cleavage under a specific set of conditions. The majority of the prior art on cleavable epoxy compositions has been focused on incorporation of different cleavable groups in the resin component. Such reports are also geared toward the use of epoxy as a reworkable adhesive for electronics applications that allow glued or encapsulated components to be debonded under a specific set of conditions. Selected examples of such reworkable epoxy compositions include U.S. Pat. Nos. 5,932,682, 5,560,934, and 5,512,613, each referring to a reworkable epoxy thermosetting composition based on a diepoxide component in which the moiety connecting the two epoxy groups is an acid labile acyclic ketal or acetal linkage. The cured resins are shown to be useful for adhesives and for electronic encapsulates for use as removable electronic encapsulation. The anhydride-cured resins are shown to disassemble in acidic environments.

U.S. Pat. No. 6,887,737 B1 refers to a reworkable epoxy thermosetting composition based on a resin component that contains at least two cleavable acetal or thioacetal linkages. The described epoxy compositions are thermally reworkable.

U.S. Pat. No. 6,657,031B1 describes thermally reworkable epoxy compositions for use in electronic underfills based on a diepoxide component that contains thermally labile ester linkages, allowing bonded electronic components to more easily be detached after heating.

As disclosed herein for the first time, a reworkable epoxy composition that is designed to have cleavable linkages in the hardener components, as opposed to the resin component, is more attractive on both performance and economic grounds. The skilled artisan will understand that hardener components of epoxy compositions are often interchanged. The skilled artisan will understand that the volume percentage of a hardener is significantly less than that of the resin component in commonly used epoxy compositions (i.e. any added cost is more diluted). The skilled artisan will understand that the industrial standard epoxy resin used for structural and composite applications is the diglycidyl ether of bisphenol A (DGEBPA) of various grades. As will be illustrated by the disclosure encompassed herein, the breaking of cross-links in reworkable epoxy compositions derived from amino curing agents with cleavable linkages and diepoxide resins can lead to the formation of linear polymers. The present disclosure thereby provides a mechanism for the transformation of a thermosetting matrix into a thermoplastic, which is a recyclable material. As disclosed herein, the molecular structure of the cleavable linkage in the hardener is paramount to the degradation ability of the theimoset matrix in the ambient environment, and just the same, the ease or difficulty of the reworkability or recycling of the cured epoxy compositions. Ideally, degradation would not occur in the materials' ambient environment, but only when recycling is selectively desirable.

International Patent Application No. PCT/CN2011/076980 discloses the use of acid liable amine hardeners for reworkable epoxy compositions. Specifically, the use of aminoacetal, aminoketal, aminoorthoester, or aminoorthocarbonate hardeners with epoxy resins is described. When immersed in acidic environments, the cross-links that make up the three-dimensional network of the cured epoxy, breakdown, and the cured-epoxy can be dissolved. The ease or difficulty of epoxy dissolution can be controlled by the type of hardener employed. International Patent Application No. PCT/CN2012/075084 discloses the use of acid liable amine hardeners for reworkable epoxy compositions containing one or more reinforcing components. When immersed in acidic environments, the cross-links that make up the three-dimensional network of the cured, reinforced epoxy break down. The cured-epoxy can be dissolved and the reinforcing components recovered. The ease or difficulty of epoxy dissolution can be controlled by the type of hardener employed.

Existing thermosetting composite recycling technology entails the incineration of the plastic constitution of the material and recovery the reinforcement fiber. In an embodiment as encompassed herein, the use of reworkable epoxy compositions to fabricate composites provides a more fully recyclable approach because it enables both plastic and fibers to be recovered from the composite. In an embodiment, the cross-linked epoxy resin degrades into epoxy-based polymers or smaller molecular fragments, which may be thermoformable and have useful properties. As will be understood by the skilled artisan, epoxy theinioplastics are engineered polymers that can be used in other industrial applications. The polymer obtained from recycling may be reused or repurposed in other applications that are well suited for thermoplastics such as powder coatings, laminates, injection molding, compression molding, etc.

In an embodiment, the combined mass recovery of the reinforcement materials and epoxy degradation material can exceed 80%, and the reinforcement material can be recovered in good form provided that it is sufficiently stable to the basic recycling conditions. In an embodiment, the recycling methods of the reworkable epoxy resin compositions and products/composite materials encompassed herein are relatively mild, economical, and easy to control. For example, the processes can be simple enough to be performed at the site of product manufacturing, whereby prost-production epoxy scrap waste could be recycled instead of being thrown in the landfill.

The economic implications of the disclosed reworkable epoxy compositions for composite product manufactures are potentially substantial, as it allows value to be extracted back from expenditures and manufacturing costs. Thus, the present disclosure meets a primary objective behind recycling—in addition to environmental protection—in that it demonstrates the breakdown of end-of-life products in to their raw material and/or high value material that can be reused to make new products. It also fulfills the long-term goals of the cradle-to-cradle life cycle in that it helps promote recycling as a prime alternative source to raw materials.

This disclosure relates, in part, to processes for the preparation of polyaminoacetals, including the compound of formula (I), also known as di-(2-aminoethyl) formal acetal:

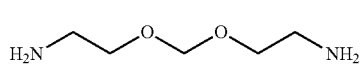

Formula (I)

In an embodiment, encompassed herein are processes for the preparation di-(2-aminoethyl) formal (Formula I).

Formula I contains an acetal group, specifically a formal group, which links two primary amine end groups. Because Formula I contains two primary amine groups, it can be used to make polymeric materials (e.g., nylons) or cross-linked polymers such as epoxies or polyurethanes, by way of several non-limiting examples. Polymeric materials derived from Formula I may be degradable under acidic conditions by way of the acetal linkage, which is acidic labile. Degradable polymeric materials may have a variety of applications. A synthetic process for the preparation of di-(2-aminoethyl) formal that is both economical and amenable to multi-ton scale synthesis could enable the cost-effective manufacture of degradable materials. Encompassed herein are multiple different synthetic routes that may be used for the preparation of di-(2-aminoethyl) formal.

In an embodiment, a direct and economical route for the preparation of Formula I is a single-step sequence involving the direct reaction of ethanolamine with formaldehyde. However, this process does not lead to the formation of I, but instead leads to the production of a 1,3,5-triazine (Formula II) as show in scheme 1.

Scheme 1

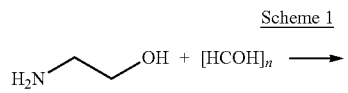

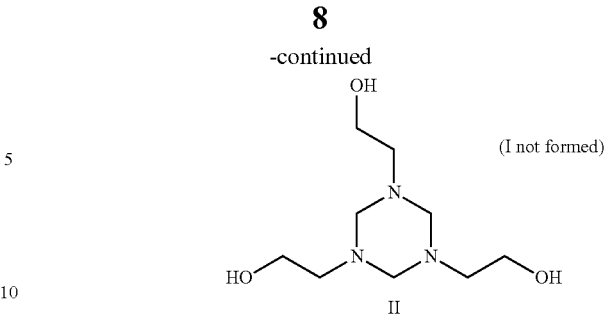

The production of Formula II can easily be rationalized by the fact that the more reactive amino group of ethanolamine reacts with formaldehyde, instead of the less reactive hydroxyl group. Suitably protected ethanolamine derivatives, such as, but not limited to, N-(2-hydroxyethyl)phthalimide, can be used in place of ethanolamine to provide Formula I in a two step sequence as is shown in scheme 2. This general approach is the most used method for the preparation of Formula I in the prior art as is documented, for example, in U.S. Pat. No. 5,191,015. The reported overall yield for this sequence is generally in the range of 50-60%. While this documented procedure is relatively straightforward to perform in the laboratory setting, the process is not ideal for a multi-ton industrial process. The method is not atom economical as nearly 5 ton of the N-(2-hydroxyethyl)phthalimide (III) starting material would be required for the production of every 1 ton of Formula I.

Scheme 2

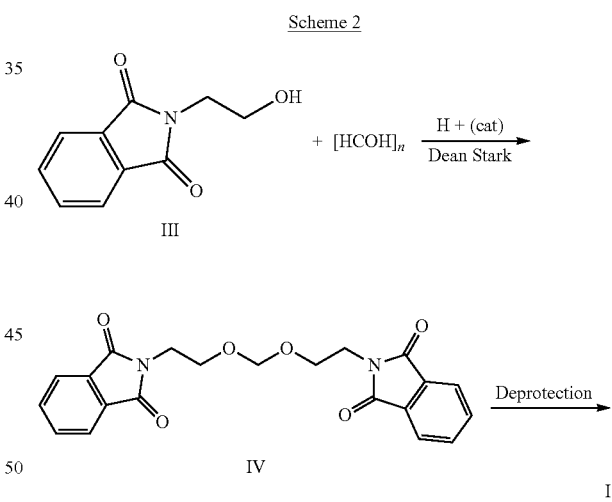

U.S. Pat. No. 2,409,675 is the other documented process for the preparation of di-(2-aminoethyl) formal of Formula I in the prior art. The patent discloses preparation of Formula I via a multi-step method that generally entails: 1) the reaction of glyconitrile with excess of an acetal; 2) hydrogenation of the resulting unsymmetrical cyanoacetal in the presence of ammonia and a hydrogenation catalyst; 3) treatment of the unsymmetrical cyanoacetal with excess of acid, which promotes a disproportiaonation reaction and leads to the salt of di-(2-aminoethyl) formal; and 4) isolation of I after deprotonation with a base. U.S. Pat. No. 2,409,675 discloses a multi-step chemical synthesis of di-(2-aminoethyl) formal acetal (I) according to the following Scheme 3;

Scheme 3

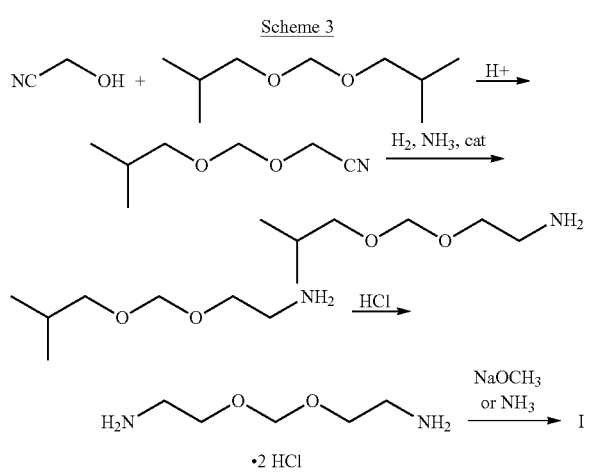

The invention is further described by the following examples. It should be recognized that variations based on the inventive features are within the skill of the ordinary artisan, and that the scope of the invention should not be limited by the examples. To properly determine the scope of the invention, an interested party should consider the claims herein, and any equivalent thereof. In addition, all citations herein are incorporated by reference, and unless otherwise expressly stated, all percentages are by weight.

In another embodiment, encompassed herein are processes for the preparation di-(3-aminopropyl) formal (Formula X).

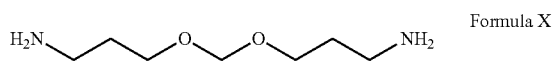 [SMILES: NCCCOCOCCCN]

Formula X contains an acetal group, specifically a formal group, which links two primary amine end groups. Because Formula X contains two primary amine groups, it can be used to make polymeric materials (e.g., nylons) or cross-linked polymers such as epoxies or polyurethanes, by way of a few non-limiting examples. Polymeric materials derived from Formula X may be engendered with the property of degradability under acidic conditions because the said compound contains an acetal linkage, which is acidic labile. Degradable polymeric materials may have a variety of applications. A synthetic process for the preparation of di-(3-aminopropyl) formal that is both economical and amenable to multi-ton scale synthesis could enable the cost-effective manufacture of degradable materials. In an embodiment, the disclosure encompassed herein describes several different synthetic routes that may be used for the preparation of di-(3-aminopropyl) formal.

Given various shortcomings of the known processes for making di-(2-aminoethyl) formal acetal, a need exists for economical and scalable synthetic processes for the preparation of di-(2-aminoethyl) formal acetal and related compounds. As described herein, the disclosure encompassed herein now provides multiple processes for the preparation of the molecules described herein, with advantageous results over the methods previously known in the art.

In an aspect the present invention provides a set of processes of chemical synthesis that may be used for the preparation of polyaminoacetals. In an embodiment, a process of chemical synthesis of di-(2-aminoethyl) formal acetal I is described. In one embodiment, said process comprises reacting a compound of formula Va with a second compound selected from the group consisting of ammonia, ammonium salt, and combinations or equivalents (such as ammonium hydroxide) thereof, to form a compound formula I, wherein $L^1$ and $L^2$ are the same or different and each is independently a leaving group or leaving group precursor.

Scheme 4.

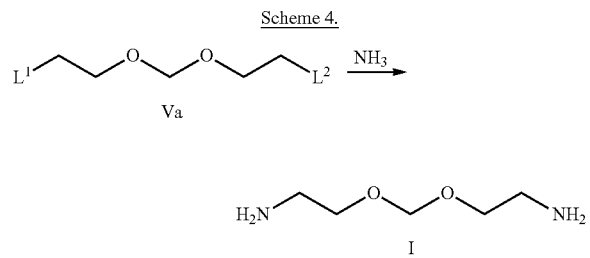

In an embodiment, each of $L^1$ and $L^2$ is independently selected from the group consisting halogen or an alkyl- or aryl-sulfonyloxy group. In an embodiment, each of $L^1$ and $L^2$ is independently selected from the group consisting of a chloro, a bromo, an iodo, a mesyloxy, a besyloxy and a tosyloxy group. In another embodiment, each of $L^1$ and $L^2$ is independently selected from the group consisting of a halide, methanesulfonate, para-toluenesulfonate, trifluoromethane sulfonate, mono nitro and dinitro phenolate.

In some embodiments, said process of chemical synthesis of di-(2-aminoethyl) formal acetal I further comprises adding an additive to the reaction. In one embodiment, said additive is an iodide salt. In a further embodiment, said iodide salt is a potassium iodide or a sodium iodide or a combination of both.

In an embodiment, the substitution reaction is conducted at a temperature range of from about 0° C. to 200° C. In an embodiment, the substitution reaction is conducted at a temperature range of from about 40° C. to 140° C. In another embodiment, the substitution reaction is optionally conducted in the presence of a solvent. In another embodiment, the substitution reaction is optionally conducted in the presence a solvent is selected from the group consisting of, but not limited to, water, methanol, ethanol, dioxane and combinations thereof. In an embodiment, the substitution reaction is conducted in a pressurized system, at a pressure selected based on the desired reaction properties and results. In an embodiment, the substitution reaction is conducted in the presence of excess ammonia or ammonia equivalents. In one embodiment, the molar proportion of ammonia or ammonia equivalent to the compound of formula (5) is about 20:1. In another embodiment, the molar proportion of ammonia or ammonia equivalent to the compound of formula Va is greater than about 20:1. In another embodiment, the molar proportion of ammonia or ammonia equivalent to the compound of formula Va is less than about 20:1.

In an embodiment, I is isolated by distillation of the reaction mixture. In another embodiment, I is isolated by extracting the reaction mixture with a solvent followed by evaporation of the solvent and/or distillation of the extract.

In some exemplary embodiments of a process of chemical synthesis of di-(2-aminoethyl) formal acetal I, the process comprises reducing di-(2-nitroethyl) formal acetal Vb with a reducing agent to form the compound formula I as shown in scheme 5 below:

Scheme 5.

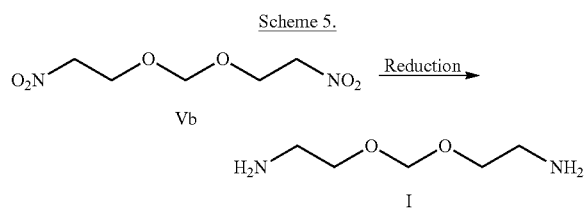

In an embodiment, the reducing agent is hydrogen gas in the presence of a catalyst. In one embodiment, reducing agent is selected from the group consisting of hydrogen in the presence of catalytic Raney nickel, hydrogen in the presence of catalytic Palladium on carbon (Pd/C), catalytic Pd/C and ammonium formate in methanol, hydrogen in the presence of catalytic $PtO_2$, iron metal in the presence of acid, and iron metal/$FeCl_3$ in the presence of acid.

In another embodiment, the hydrogenation catalyst is recovered and recycled. In another embodiment, the hydrogenation is recovered via filtration after the reaction is complete. In an embodiment, the reaction is conducted at a temperature range of from about 20° C. to 200° C. In an embodiment, the reaction is conducted at a temperature range of from about 40° C. to 140° C. As will be understood based on the disclosure set forth herein, the selected temperature may vary depending upon the catalyst used, etc. . . . In an embodiment, I is isolated by distillation of the reaction mixture. In another embodiment, I is isolated by extracting the reaction mixture with a solvent followed by evaporation of the solvent and/or distillation of the extract. In another embodiment, I is isolated by filtration of the reaction mixture followed by distillation of the filtrate.

In some embodiments, the reaction is conducted under hydrogen gas pressure of from about 1 atm to about 1000 atm.

In some exemplary embodiments of a process of chemical synthesis of di-(2-aminoethyl) formal acetal I, said process comprising reacting ethanolamine with paraformaldehyde or any suitably masked formaldehyde equivalent in the presence of an acid to form di-(2-aminoethyl) formal acetal salt VII; and reacting said di-(2-aminoethyl) formal acetal salt VII with a base to form di-(2-aminoethyl) formal acetal I as shown in scheme 6 below.

Scheme 6

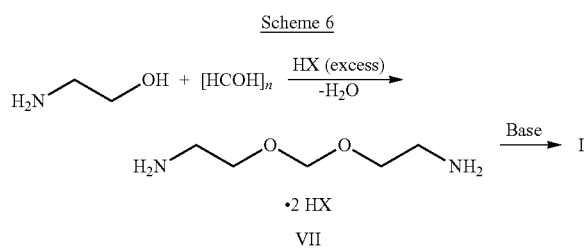

In one embodiment, said acid is an inorganic acid. In another embodiment, said acid is selected from the group consisting of HCl, HBr and $H_2SO_4$. In an embodiment, said acid is an organic acid. In another embodiment, said organic acid is p-toluenesulfonic acid, acetic acid, or methanesulfonic acid.

In one embodiment, the suitably masked formaldehyde equivalent is trioxane. In another embodiment, the ratio of the molar equivalence of the acid to ethanolamine is greater than 1. In some embodiments, ethanolamine is pretreated with an acid prior to the reaction with the paraformaldehyde or the any suitably masked formaldehyde equivalent.

In some embodiments, the process of chemical synthesis of scheme 6 further comprises an adding a drying agent to the reaction mixture. In one embodiment, said drying agent is anhydrous magnesium sulfate ($MgSO_4$). In another embodiment, said drying agent is sodium sulfate ($Na_2SO_4$) or potassium sulfate ($K_2SO_4$). In some embodiments, the process of chemical synthesis of scheme 6 is conducted under Dean-Stark type reaction condition to remove any water formed during the reaction. In some embodiments, the process of chemical synthesis of scheme 6 is conducted at temperature ranging from about 0° C. to about 220° C.

In some exemplary embodiments, a process of chemical synthesis of the present invention comprises reacting ethanolamine with a formylacetal VIII to form di-(2-aminoethyl) formal acetal salt VII; and reacting said di-(2-aminoethyl) formal acetal salt VII with a base to form di-(2-aminoethyl) formal acetal I as shown in scheme 7 below.

Scheme 7

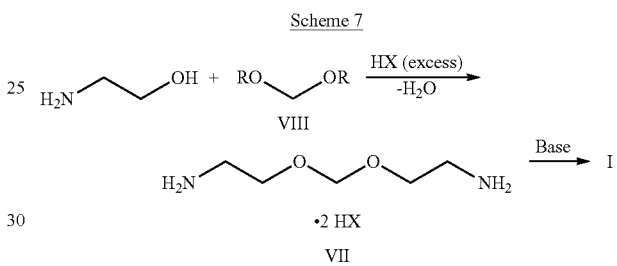

Example 1

Preparation of I Via the Ammonolysis of Di-(2-Chloroethyl) Formal (Formula V)

The key embodiment of this example is the formation of Formula I via the ammonolysis of di-(chloroethyl) formal (Formula V).

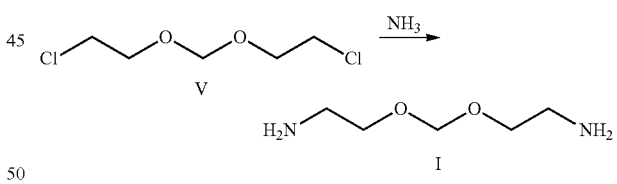

The synthesis of Formula V can be readily achieved from the reaction of 2-chloroethanol and formaldehyde (which can be employed in solid form as paraformaldehyde or trioxane), which are relatively inexpensive raw materials. There are well established processes for the preparation of Formula V, which are suitable for large scale preparation. The key reaction of this example is the alkylation reaction between 2 equivalents of ammonia and Formula V to form Formula I. In an embodiment, this reaction can be carried out according to standard reaction protocols that involve the reaction of an alkyl chloride with ammonia or ammonia equivalent like ammonium hydroxide. In an embodiment, the reaction is amenable to being carried out in a pressure vessel in a batch process, or in a continuous reactor in a continuous process. In an embodiment, Formula I can be prepared by the reaction of di-(2-chloroethyl) formal Formula V with an excess of anhydrous liquid NH₃ in an autoclave reactor or under pressurized conditions, such as in a pressure vessel. NH₃ should be used in excess to minimize the amount of multiple alkylation byproducts. In the case of a dialkyl chloride like Formula V, multiple alkylation would lead to the formation of oligomers (or even crosslinking). While the complete avoidance of such byproducts may be unavoidable in the ammonolysis of Formula V, Formula I may still be obtained in sufficient purity via distillation due to its lower vapor pressure (relative to its oligomeric counterparts). The preferred molar proportion of NH₃/Formula V is 20:1, but in various embodiments, this ratio can be greater than or less than 20:1. While in preferred embodiments, the reaction is carried out without a solvent, in other embodiments, the reaction may be carried out in a solvent. Non-limiting examples of optional solvents include, independently or in combination, water, methanol, ethanol, and dioxane. The reaction can be carried out in the range from 20° C. to 200° C., and in an embodiment, in the range of 40° C. to 140° C. In an embodiment, the reaction time and yield may be increased by the addition of additives, such as, but not limited to, NaI. In an embodiment, upon completion of the reaction, any excess of ammonia can be released. In an embodiment, the ammonia can be captured for recycling. Formula I can be isolated via distillation after filtration of NH₄Cl or other salts. In an embodiment, molecular species having basic pH characteristics can be added to aid in purification. In another embodiment, Formula I can be purified via an extraction process and subsequent distillation.

Example 2

Preparation of Formula I Via the Reduction of Di-(2-Nitroethyl) Formal (Formula VI)

The key embodiment of this example is the formation of Formula I via the reduction of di-(2-nitroethyl) formal (Formula VI).

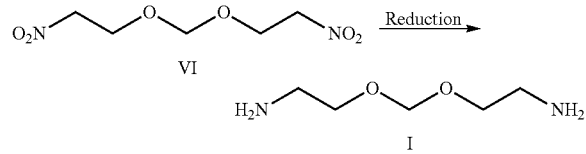

The synthesis of Formula VI can be accomplished via the reaction of 2-nitroethanol and formaldehyde (which can be employed in solid form as paraformaldehyde or trioxane) such as using the procedures detailed for dinitro acetal compounds in U.S. Pat. No. 2,415,046 or U.S. 2009/0216049 A1. There are a variety of common conditions used by those skilled in the art for the reduction of aliphatic nitro compounds to the corresponding amines. The conversion of Formula VI to Formula I may be accomplished using such protocols. By way of a non-limiting example, such protocols include catalytic hydrogenation reaction using Raney nickel, catalytic hydrogenation reaction using Palladium on carbon (Pd/C), catalytic reduction using Pd/C and ammonium formate in methanol, catalytic hydrogenation using PtO₂, catalytic hydrogenation using other efficient hydrogenation catalyst for the reduction of aliphatic nitro groups to their corresponding amines, reduction using iron metal in the presence of acid, reduction using iron metal/FeCl₃ in the presence of acid. In an embodiment, the hydrogenation catalyst may be recovered via filtration after the reaction is complete. In an embodiment, the hydrogenation catalyst may be recycled. In an embodiment, Formula I can be isolated via distillation. In an embodiment, Formula I can be purified via an extraction process and can optionally be further purified via distillation.

Example 3

Preparation Of Formula I from Ethanolamine and Formaldehyde with Excess Acid

Ethanolamine is an inexpensive feedstock chemical that is readily available in mass quantities. As discussed elsewhere herein, the direct reaction of formaldehyde with ethanolamine does not lead to the formation of Formula I. This is because of the increased reactivity of the amino group relative to the hydroxyl group. Suitably protected ethanolamine derivatives such as N-(2-hydroxyethyl)phthalimide can be used in place of ethanolamine to obtain Formula I in a two step sequence as in Scheme 2. In an embodiment, ethanolamine can be successfully reacted with formaldehyde (which can be employed in solid form as paraformaldehyde or trioxane) to obtain Formula I, provided that the reaction is carried out in an excess of acid (i.e., the molar equivalence of acid:ethanolamine is greater than 1). In an embodiment, when the reaction of ethanolamine with formaldehyde is carried out in the presence of an excess of strong acid, the reactive lone pair of the nitrogen group in ethanolamine is predominately in the protonated form, effectively inhibiting its ability to react with the aldehyde. In this way, the hydroxyl group of ethanolamine is then able to react with the aldehyde. Thus, two equivalents of the protonated form of ethanolamine can react with formaldehyde to yield Formula VII, which is the doubly protonated salt of I.

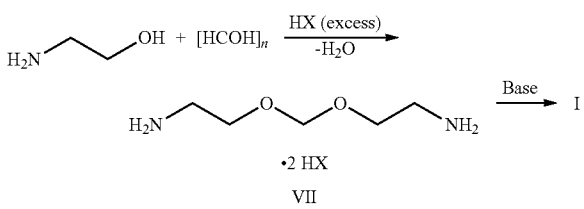

In an embodiment, deprotonation of Formula VII with a base then provides Formula I. In a preferred embodiment, ethanolamine is treated with acid prior to the addition of the formaldehyde species. Non-limiting examples of suitable acids include inorganic acids such as HCl and H₂SO₄, or organic acids such as p-toluenesulfonic acid or methanesulfonic acid. In an embodiment, formation of VII can be greatly facilitated by conditions that remove the formed water during the reaction. In an embodiment, removal of formed water can be accomplished by the addition of drying agents such as MgSO₄ to the reaction mixture. In another embodiment, removal of the water is effected via use of Dean-Stark type conditions. The reaction temperature can be in the range from 0° C. to 220° C. In an embodiment, ethanolamine hydrochloride is commercially available and it can be used in lieu of the in situ protonation of ethanolamine. Ethanolamine hydrochloride is a low melting solid and it can be reacted with paraformaldehyde (or trioxane) in the melt, and water removed via distillation. In an embodiment, conversion of Formula VII to Formula I can be accomplished by removal of any volatiles and by treatment with a base. In an embodiment, Formula I may be further purified via extraction techniques or by distillation.

Example 4

Preparation of Formula I from Ethanolamine and an Acetal of Formaldehyde with Excess Acid The embodiments of this example follow those of Example 3 with the substitution of an acetal of formaldehyde (Formula VII) used in place of formaldehyde. Non-limiting examples of suitable acetals include Formula VII; wherein R=alkyl or substituted alkyl group.

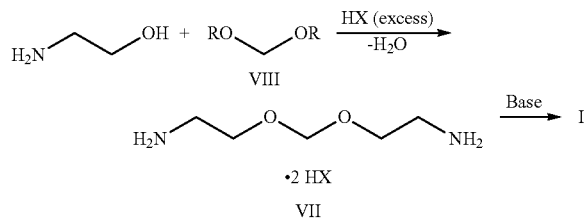

Example 5

Preparation of Formula X Via Catalytic Hydrogenation of the Formal of Ethylene Cyanohydrin (Formula XI)

The key embodiment of this example is the formation of Formula X via catalytic hydrogenation of the formal of ethylene cyanohydrin (Formula XI).

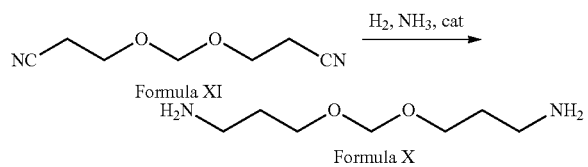

The starting compound Formula XI for this transformation can be prepared from the reaction of 2 molar equivalents of acrylonitrile with 1 molar equivalents of paraformaldehyde under aqueous reaction conditions. The key reaction of this disclosure is the transformation of the dinitrile Formula XI to the diamine Formula X. In an embodiment, this transformation may be accomplished using standard reaction protocols used for the reduction of aliphatic nitrile compounds to their corresponding amines in the art. In an embodiment, the transformation is carried out via a catalytic hydrogenation reaction. In an embodiment, the conversion of Formula X to Formula XI may be effected in the liquid phase employing a suitable active hydrogenation catalyst. In an embodiment, conventional hydrogenation catalysts include as the active component a noble metal from the group Ru, Rh, Pd, and Pt, or a transition metal the group Cu, Cr, Co, Ni, Fe, including, but not limited to, Raney catalysts and chromite catalyst. In an embodiment, bimetallic catalysts of one or more transition metals and/or noble metals may also be used. One of skill in the art, when viewing the present disclosure, will understand how to select a catalyst, including considerations of the useful life of any particular catalyst. In an embodiment, an example of a preferred catalyst is Raney Ni. In an embodiment, the hydrogenation can be conducted in the liquid or vapor phase at temperatures ranging between 20° C. and 200° C. and at pressures of 1 and 1000 atmospheres, and in another embodiment, in the temperate range between 60° C. and 150° C. and under pressures between 10 and 110 atmospheres. In an embodiment, the conversion of Formula X to Formula XI may be enhanced by the presence of ammonia during the reaction. In an embodiment, from 1 to 20 moles of ammonia per mole of Formula X is used. In an embodiment, hydrogenation of Formula XI can be carried out using anhydrous ammonia. In an embodiment, hydrogenation is carried out in aqueous ammonia, or in a suitable solvent such as, but not limited to, for example, methanol, ethanol, dioxane, or any solvent that is not substantially hydrogenated during the reaction or decomposed by the added ammonia. Upon the completion of the reaction, the catalyst can be removed via filtration and Formula X can be obtained after removal of any solvents. In an embodiment, Formula X can be further purified via distillation under reduced pressure.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

Each and every patent, patent application, and non-patent publication referenced herein is hereby incorporated in its entirety herein.

What is claimed is:

1. A process of chemical synthesis for the preparation of di-(3-aminopropyl) formal acetal X:

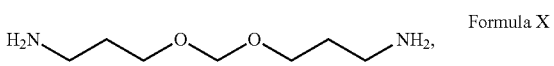

said process comprising catalytic hydrogenation of a compound of formula

IX:

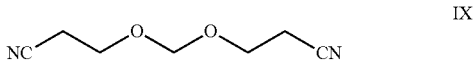

to produce the di-(3-aminopropyl) formal acetal X.

2. The process of chemical synthesis of claim 1, wherein 2 molar equivalents of the compound of formula IX and 1 molar equivalent of paraformaldehyde are used.

3. The process of chemical synthesis of claim 1, wherein the catalytic hydrogenation occurs under aqueous reaction conditions.

4. The process of chemical synthesis of claim 1, wherein the catalytic hydrogenation uses a catalyst including, as an active component, a metal selected from the group consisting of Ru, Rh, Pd, and Pt.

5. The process of chemical synthesis of claim 1, wherein the catalytic hydrogenation uses a catalyst including, as an active component, a metal selected from the group consisting of Cu, Cr, Co, Ni, and Fe.

6. The process of chemical synthesis of claim 1, wherein the catalytic hydrogenation uses a catalyst including, as an active component, a bimetallic catalyst comprising one or more transition metals and/or noble metals.

7. The process of chemical synthesis of claim 1, wherein the catalytic hydrogenation is conducted in liquid phase.

8. The process of chemical synthesis of claim 1, wherein the catalytic hydrogenation is conducted at temperatures between 20° C. and 200° C.

9. The process of chemical synthesis of claim 1, wherein the catalytic hydrogenation is conducted at hydrogen pressure between 1 and 1000 atmospheres.

10. The process of chemical synthesis of claim 1, wherein the catalytic hydrogenation is conducted at a temperate between 60° C. and 150° C.

11. The process of chemical synthesis of claim 1, wherein the catalytic hydrogenation is conducted under hydrogen pressure between 10 atmospheres and 110 atmospheres.

12. The process of chemical synthesis of claim 1, wherein the catalytic hydrogenation is conducted in the presence of ammonia.

13. The process of chemical synthesis of claim 12, wherein the ammonia is present in an amount between 1 mole to 20 moles per mole of the compound of Formula IX used.

14. The process of chemical synthesis of claim 1, wherein the catalytic hydrogenation is conducted in the presence of anhydrous ammonia.

15. The process of chemical synthesis of claim 1, wherein the catalytic hydrogenation is conducted in the presence of aqueous ammonia.

16. The process of chemical synthesis of claim 1, wherein the catalytic hydrogenation is conducted in the presence of a solvent selected from the group consisting of methanol, ethanol, and dioxane.

17. The process of chemical synthesis of claim 1, further comprising removing hydrogenation catalyst.

18. The process of chemical synthesis of claim 17, wherein the hydrogenation catalyst is removed via filtration.

19. The process of chemical synthesis of claim 1, further comprising purifying di-(3-aminopropyl) formal acetal of formula X.

20. The process of chemical synthesis of claim 19, wherein di-(3-aminopropyl) formal acetal X is purified via distillation.

21. The process of chemical synthesis of claim 20, wherein the distillation is conducted under reduced pressure.

22. The process of chemical synthesis of claim 1, wherein the catalytic hydrogenation uses a catalyst selected from the group consisting of Raney catalysts and chromite catalysts.

* * * * *